(12) United States Patent
Song et al.

(10) Patent No.: US 9,995,625 B2
(45) Date of Patent: Jun. 12, 2018

(54) DEVICE FOR GENERATING AND DETECTING PHOTO MIXING-TYPE CONTINUOUS-WAVE TERAHERTZ USING PHASE NOISE COMPENSATION METHOD

(71) Applicant: GWANGJU INSTITUTE OF SCIENCE AND TECHNOLOGY, Gwangju (KR)

(72) Inventors: Jongin Song, Gwangju (KR); Hajun Song, Gwangju (KR)

(73) Assignee: GWANGJU INSTITUTE OF SCIENCE AND TECHNOLOGY (KR)

( * ) Notice: Subject to any disclaimer, the term of this patent is extended or adjusted under 35 U.S.C. 154(b) by 0 days. days.

(21) Appl. No.: 15/516,671

(22) PCT Filed: Oct. 2, 2015

(86) PCT No.: PCT/KR2015/010442
§ 371 (c)(1),
(2) Date: Apr. 3, 2017

(87) PCT Pub. No.: WO2016/053049
PCT Pub. Date: Apr. 7, 2016

(65) Prior Publication Data
US 2017/0292875 A1    Oct. 12, 2017

(30) Foreign Application Priority Data
Oct. 2, 2014    (KR) .................. 10-2014-0133121

(51) Int. Cl.
*G01J 3/10*    (2006.01)
*G01N 21/3581*    (2014.01)
(Continued)

(52) U.S. Cl.
CPC .......... *G01J 3/108* (2013.01); *G01N 21/3581* (2013.01); *G01N 21/39* (2013.01);
(Continued)

(58) Field of Classification Search
CPC ...... G01J 3/108; H01S 3/2308; H01S 3/0085; G01N 21/39; G01N 21/3581; G01N 2201/067; G01N 2201/06113
(Continued)

(56) References Cited

U.S. PATENT DOCUMENTS

| 6,388,799 B1 * | 5/2002 | Arnone | G01N 21/3581 |
| | | | 359/326 |
| 9,857,217 B2 * | 1/2018 | Wakatsuki | G01J 1/44 |

(Continued)

FOREIGN PATENT DOCUMENTS

| JP | 2007-071704 A | 3/2007 |
| JP | 2013-032933 A | 2/2013 |

(Continued)

OTHER PUBLICATIONS

International Search Report for PCT/KR2015/010442 dated Feb. 3, 2016.

*Primary Examiner* — David Porta
*Assistant Examiner* — Gisselle Gutierrez
(74) *Attorney, Agent, or Firm* — Steven M. Greenberg; CRGO Law (57) ABSTRACT

An embodiment of the present invention provides a continuous-wave terahertz generation and detection device using a photomixing technique, the device including: first and second light source units configured to output continuous-wave laser light sources, which have single wavelength and different frequencies, to generate optical signals; a first electro-optic phase modulator configured to shift a fre- (Continued)

quency of the optical signal generated by the first light source unit, and a second electro-optic phase modulator configured to shift a frequency of the optical signal generated by the second light source unit; a first optical amplifier configured to receive and amplify the optical signal whose frequency is shifted by the first electro-optic phase modulator and the optical signal generated by the second light source unit, and a second optical amplifier configured to receive and amplify the optical signal whose frequency is shifted by the second electro-optic phase modulator and the optical signal generated by the first light source unit; an opto-electronic converter configured to convert the optical signal amplified by the first optical amplifier into a terahertz wave; a photomixer configured to mix the optical signal amplified by the second optical amplifier and the terahertz wave generated by the opto-electronic converter and convert the mixed signal into an electrical signal; a photodetector configured to combine the optical signals transferred from the first and second optical amplifiers and convert the combined optical signal into an electrical signal; and a filter unit configured to filter the electrical signal passing through the photodetector, wherein the electrical signal obtained through the photodetector is compared with the electrical signal obtained by the photomixer, and phase noise having the same frequency is removed.

9 Claims, 4 Drawing Sheets (51) Int. Cl.
G01N 21/39 (2006.01)
H01S 3/00 (2006.01)
H01S 3/23 (2006.01)

(52) U.S. Cl.
CPC .......... *H01S 3/0085* (2013.01); *H01S 3/2308* (2013.01); *G01N 2201/067* (2013.01); *G01N 2201/06113* (2013.01)

(58) Field of Classification Search
USPC ........................................................ 250/338.1
See application file for complete search history.

(56) References Cited

U.S. PATENT DOCUMENTS

| | | | |
|---|---|---|---|
| 2008/0212974 A1* | 9/2008 | Davies | H04B 10/2575 398/140 |
| 2009/0180122 A1* | 7/2009 | Federici | G01J 3/42 356/451 |
| 2010/0092183 A1* | 4/2010 | Kim | H04B 10/2575 398/183 |
| 2013/0146769 A1* | 6/2013 | Ouchi | G01J 3/42 250/338.1 |
| 2013/0156436 A1* | 6/2013 | Kim | H04B 10/90 398/115 |
| 2013/0156437 A1* | 6/2013 | Kim | H04B 10/90 398/115 |
| 2014/0231627 A1* | 8/2014 | Wakatsuki | H01Q 3/2676 250/208.2 |
| 2015/0029575 A1* | 1/2015 | Hara | G01J 3/10 359/279 |
| 2016/0109294 A1* | 4/2016 | Kasper | G01J 3/4338 250/339.07 |

FOREIGN PATENT DOCUMENTS

| | | |
|---|---|---|
| JP | 2013-507005 A | 2/2013 |
| KR | 10-2013-0064684 A | 6/2013 |
| WO | 2009-127843 A1 | 10/2009 |

* cited by examiner

The present invention is directed to provide a terahertz wave generation and detection device capable of minimizing phase noise, which is caused by a change in a temperature of a measurement system, by simply matching lengths of effective optical lines which are provided in the continuous-wave terahertz generation and detection device and through which two optical signals pass.

Technical Solution

In one embodiment, a continuous-wave terahertz generation and detection device includes: first and second light source units including single-wavelength laser light sources having different frequencies; a first electro-optic phase modulator configured to shift a frequency of a laser optical signal output from the first light source unit, and a second electro-optic phase modulator configured to shift a frequency of a laser optical signal output from the second light source unit; a first optical amplifier configured to receive and amplify the optical signal whose frequency is shifted by the first electro-optic phase modulator and the optical signal output from the second light source unit, and a second optical amplifier configured to receive and amplify the optical signal whose frequency is shifted by the second electro-optic phase modulator and the optical signal output from the first light source unit; an opto-electronic converter configured to convert the optical signal amplified by the first optical amplifier into a terahertz wave; a photomixer configured to photomix the optical signal amplified by the second optical amplifier and the terahertz wave generated by the opto-electronic converter and convert the photomixed signal into an electrical signal; a photodetector configured to combine a portion of the optical signals output from the first and second optical amplifiers and convert the combined optical signal into an electrical signal; and a filter unit configured to filter the electrical signal converted by the photodetector, wherein the electrical signal obtained through the photodetector is compared with the electrical signal obtained by the photomixer, and phase noise having the same frequency is removed.

The optical signal amplified by the first optical amplifier may be distributed and transferred to the photodetector and the opto-electronic converter, and a size of an optical path formed between the first optical amplifier and the photodetector may be set to have the same effective optical delay time as the sum of an optical path formed between the first optical amplifier and the opto-electronic converter and an optical path through which the terahertz wave generated by the opto-electronic converter is transferred to the photomixer.

The optical signal amplified by the second optical amplifier may be distributed and transferred to the photodetector and the photomixer, and an optical path formed between the second optical amplifier and the photodetector may be set to have the same effective optical delay time as that of an optical path formed between the second optical amplifier and the photomixer.

Advantageous Effects

According to the present invention, the influence of phase noise caused by a continuous-wave laser light source can be reduced by adding a photodetector and a simple electronic circuit to a terahertz wave system.

The occurrence of a effective optical delay time difference, which is caused by a change in temperatures of various optical components for optical signal splitting, optical frequency shift, and optical signal amplification within two optical lines, and the resultant phase noise can be effectively removed through a phase noise removal process according to the present invention, thereby realizing a system that stably operates even when an ambient temperature changes.

According to the present invention, since the influence of phase noise due to a continuous-wave laser light source can be reduced by just adding one photodetector and an electronic circuit, a continuous-wave terahertz generation and detection device can be implemented by using a relatively inexpensive laser whose spectrum line width is not narrow, thereby reducing design costs of an entire system.

Also, since an alignment operation of adjusting lengths of two optical lines so as to have the same effective optical delay time is simplified, a terahertz system can be relatively easily designed.

MODE FOR CARRYING OUT THE INVENTION

Examples of various embodiments are illustrated in the accompanying drawings and described further below. It will be understood that the description herein is not intended to limit the claims to the specific embodiments described. On the contrary, it is intended to cover alternatives, modifications, and equivalents as may be included within the spirit and scope of the present invention as defined by the appended claims.

Example embodiments will be described in more detail with reference to the accompanying drawings. The present invention, however, may be embodied in various different forms, and should not be construed as being limited to only the illustrated embodiments herein. Rather, these embodiments are provided as examples so that this invention will be thorough and complete, and will fully convey the aspects and features of the present invention to those skilled in the art.

Figure 1:
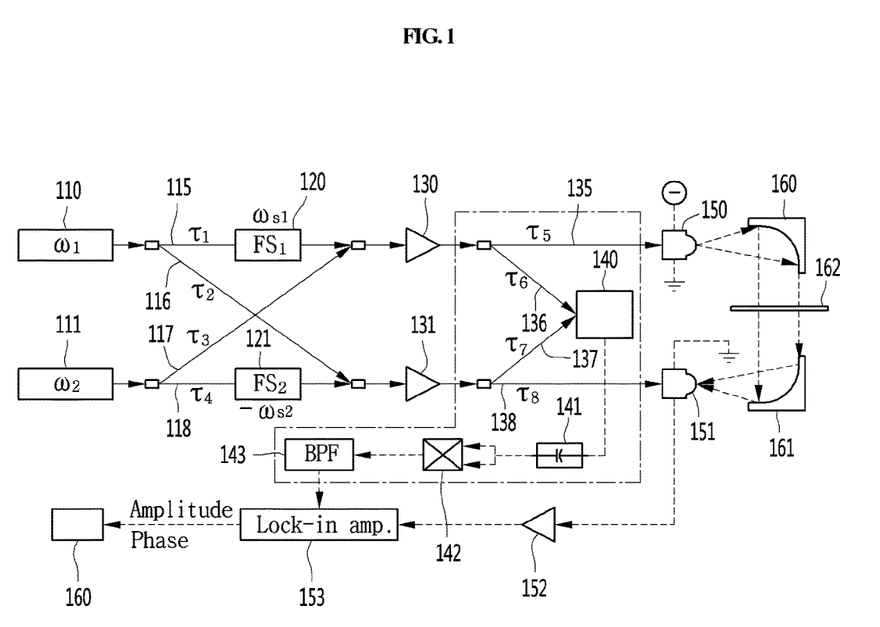
FIG. 1 is a diagram illustrating a continuous-wave terahertz generation and detection device according to an embodiment of the present invention.

FIG. 1 is a diagram illustrating a continuous-wave terahertz generation and detection device according to an embodiment of the present invention. An embodiment is a system configured by a device for generating and detecting a terahertz wave by using a photomixing technique. Since the photomixing technique provides a relatively wide terahertz signal frequency bandwidth and uses a beat frequency of two laser light sources having different wavelengths, the photomixing technique has excellent frequency variability through wavelength adjustment. Also, since the photomixing technique enables manufacturing in a semiconductor chip size and provides a high SNR, the photomixing technique is widely used for, in particular, material inspection using spectroscopy. A self-heterodyne photomixing technique is a method that can sensitively detect a phase change, and is advantageous to inspect characteristics of a low absorption material. The present embodiment proposes a continuous-wave terahertz generation and detection device using the self-heterodyne photomixing technique.

Referring to FIG. 1, the continuous-wave terahertz generation and detection device according to the embodiment is configured by adding a part indicated by a dashed line to a conventional system. For the description of the present invention, a conventional terahertz wave system except for the part indicated by the dashed line will be described briefly.

A conventional photomixing-based terahertz continuous wave generation and detection device may include: first and second light source units 110 and 111 configured to provide optical signals by using single-wavelength continuous-wave laser light sources having different frequencies $\omega_1$ and $\omega_2$; first and second electro-optic phase modulators 120 and 121 acting as a frequency shifter configured to receive one of the two optical signals and shift a frequency thereof; first and second optical amplifiers 130 and 131 configured to amplify the received continuous-wave laser light sources; an opto-electronic converter 150 configured to convert the continuous-wave laser light source amplified by the first optical amplifier 130 into a terahertz wave; and a photomixer 151 configured to receive the generated terahertz wave and convert the terahertz wave again into an electrical signal through photomixing with an output signal of the second optical amplifier.

If the first and second electro-optic phase modulators 120 and 121 modulate the optical signals into sawtooth-wave signals respectively having frequencies of $\omega_{s1}$ and $\omega_{s2}$ and amplitudes corresponding to a half-wave voltage of the electro-optic phase modulator, optical frequencies $\omega_1$ and $\omega_2$ of the output optical signals of the electro-optic phase modulators are respectively shifted by $\omega_{s1}$ and $\omega_{s1}$.

The first electro-optic phase modulator 120 is connected to the first optical amplifier 130, and the second electro-optic phase modulator 121 is connected to the second optical amplifier 131. In this case, a portion of the continuous-wave laser light source generated by the first light source unit 110 reaches the first optical amplifier 130 through the first electro-optic phase modulator 120 along an optical path 115, and another portion thereof is directly input from the first light source unit 110 to the second optical amplifier 131 along an optical path 116. Similarly, a portion of the continuous-wave laser light source generated by the second light source unit 111 reaches the second optical amplifier 131 through the second electro-optic phase modulator 121 along an optical path 118, and another portion thereof is directly input from the second light source unit 111 to the first optical amplifier 130 along an optical path 117.

For the description of the present invention, the conventional continuous-wave terahertz generation and detection device except for the part indicated by the dashed line has been described. Therefore, an effective optical delay time $\tau_1$ is an effective optical delay time related to the optical path 115, and the optical path 115 is the time taken until the optical signal travels from the first light source unit 110 through the first electro-optic phase modulator 120 and the first optical amplifier 130, is converted into the terahertz wave through the opto-electronic converter 150, and reaches the photomixer 151. $\tau_3$ is an effective optical delay time related to the optical path 117, and the optical path 117 is the time taken until the optical signal travels from the second light source unit 111 through the first optical amplifier 130, is converted into the terahertz wave through the opto-electronic converter 150, and reaches the photomixer 151. Similarly, $\tau_2$ is an effective optical delay time related to the optical path 116, and the optical path 116 is the time taken until the optical signal travels from the first light source unit 110 through the second optical amplifier 131 and reaches the photomixer 151. $\tau_4$ is an effective optical delay time related to the optical path 118, and the optical path 118 is the time taken until the optical signal travels from the second light source unit 111 through the second electro-optic phase modulator 121 and the optical amplifier 131 and reaches the photomixer 151.

A terahertz signal generated by the opto-electronic converter 150 is radiated by an antenna, and the radiated signal passes through a sample 162 by mirrors 160 and 161 and reaches the photomixer 151. The terahertz wave input after passing through the sample and the output optical signal of the second optical amplifier are photomixed by the photomixer 151. The photomixed output signal of the photomixer 151 includes a signal having a beat frequency corresponding to a shift frequency difference ($\omega_s = \omega_{s1} - \omega_{s2}$) and is amplified through a trans-impedance amplifier 152. The output signal of the photomixer 151, which has a modulation frequency difference ($\omega_s$) between the electro-optic phase modulators 120 and 121, includes signal amplitude attenuation (As) information and phase difference ($\Phi_s$) information generated by the measurement sample.

In general, since the output of the terahertz wave signal generated by the photomixing technique is at a low level and the current magnitude of the output signal generated by the photomixing in the photomixer is also small, the information can be extracted by a lock-in amplifier 153 that is used for detecting small signals. When a signal having a frequency corresponding to the modulation frequency difference ($\omega_s$) is used as a reference signal in the lock-in amplifier, it is possible to individually extract the signal amplitude attenuation (As) information and the phase difference ($\Phi_s$) information generated by the sample and included in the output signal generated by the photomixing in the photomixer.

The conventional continuous-wave terahertz generation and detection device described above has poor phase noise characteristics and thus has a lot of problems in applying to application fields that use the phase information. The reason why the conventional continuous-wave terahertz generation and detection device has poor phase noise characteristics is as follows. When the general continuous-wave laser light source includes phase noise and the effective optical delay times $\tau_1$, $\tau_2$, $\tau_3$, and $\tau_4$ of the signals passing through the effective optical lines 115, 116, 117, and 118 are different from one another, phase noise of the continuous-wave laser light source appears in the output signal of the photomixer that is generated by the photomixing. Thus, the SNR for the phase information of the system is reduced and the signal phase detection performance of the system is degraded.

In order to solve such problems, the present invention proposes a method that removes the phase noise of the output signal of the photomixer, which is generated through the photomixing, by generating the same phase noise as the phase noise of the terahertz wave generated by non-uniform effective optical lines and effective optical delay times and offsetting the phase noise through signal processing at a low frequency, thereby improving the SNR for phase information of the system and the signal phase detection performance of the system.

In the embodiment of the present invention, which includes the part indicated by the dashed line of FIG. 1, a photodetector 140 is further provided after the first and second optical amplifiers 130 and 131 provided in the conventional continuous-wave terahertz generation and detection device, and filter units 141, 142, and 143 connected to the photodetector 140 are provided. Specifically, the filter units may include a high pass filter 141 configured to remove unnecessary DC components, an electrical mixer 142 configured to mix signals filtered through the high pass filter, and a band pass filter 143 configured to detect a specific band signal by using a signal generated by the electrical mixer.

The signal obtained by the band pass filter 143 and the signal obtained by the trans-impedance amplifier 152 have the same frequency and similar phase and phase noise. In this case, if optical delays $\tau_5$ and $\tau_6$ due to the optical paths 135 and 136 connected to the optical amplifier 130 are equal to optical delays $\tau_7$ and $\tau_8$ due to the optical paths 137 and 138 connected to the optical amplifier 131, the signal obtained by the band pass filter 143 and the signal obtained by the trans-impedance amplifier 152 have the same phase noise. In a case where the phase noises of the two signals are equal to each other, if the two signals are respectively used as the measurement signal and the reference signal of the lock-in amplifier 153, it is possible to obtain phase information in which phase noise is removed from the signal obtained by the trans-impedance amplifier 152 through a lock-in process.

Next, a method of removing phase noise by using the photomixing-based continuous-wave terahertz generation and detection device proposed as above will be described.

Referring to FIG. 1 again, the first light source unit 110 and the second light source unit 111, which are two light source units having different wavelengths, generate continuous-wave laser lights having frequencies of $\omega_1$ and $\omega_2$. The frequencies of the laser lights generated by the light source units 110 and 111 are respectively shifted by $\omega_{s1}$ and $\omega_{s2}$ by the first electro-optic phase modulator 120 connected to the first light source unit 110 and the second electro-optic phase modulator 121 connected to the second light source unit 111.

The first electro-optic phase modulator 120 is connected to the first optical amplifier 130, and the second electro-optic phase modulator 121 is connected to the second optical amplifier 131. In this case, a portion of the continuous-wave laser light source generated by the first light source unit 110 reaches the first optical amplifier 130 through the first electro-optic phase modulator 120 along the optical path 115 having the delay time $\tau_1$, and another portion thereof is directly input from the first light source unit 110 to the second optical amplifier 131 along the optical path 116 having the delay time $\tau_2$. Similarly, a portion of the continuous-wave laser light source generated by the second light source unit 111 reaches the second optical amplifier 131 through the second electro-optic phase modulator 121 along the optical path 118 having the effective optical delay time $\tau_4$, and another portion thereof is directly input from the second light source unit 111 to the first optical amplifier 130 along the optical path 117 having the effective optical delay time $\tau_3$.

The light having reached the first optical amplifier 130 is converted into a terahertz wave by the opto-electronic converter 150 along the optical path 135 having the effective optical delay time $\tau_5$, passes through the sample 162, and is then input to the photomixer. The light having reached the second optical amplifier 131 is input to the photomixer 151 along the optical line 138 having effective optical delay time $\tau_8$. In this case, the optical path 135 having the delay time $\tau_5$ means an optical path formed in a section in which the light amplified by the first optical amplifier 130 is input to the photomixer 151 through the opto-electronic converter 150, and the optical line 138 having the delay time $\tau_8$ means an optical path formed in a section in which the light amplified by the second optical amplifier 131 is input to the photomixer 151.

The lights amplified by the first and second optical amplifiers 130 and 131 are input to the photodetector 140 along the optical paths 136 and 137 having the delay times $\tau_6$ and $\tau_7$, respectively. The optical paths 136 and 137 having the delay times $\tau_6$ and $\tau_7$ are optical paths formed between the first and second optical amplifiers 130 and 131 and the photodetector 140.

Signals having various frequencies may be obtained by the photodetector 140. However, since a frequency bandwidth of the photodetector 140 is not high, only the signal components $\omega_{s1}$ and $\omega_{s2}$ having low frequencies are converted into electrical signals.

After the high pass filter 141 removes the DC component from the electrical signal converted by the photodetector 140, the electrical signal is input to the electrical mixer 142 and then mixed. In this case, the electrical signal obtained by the electrical mixer 142 is composed of a DC component and a signal having a frequency of $(\omega_{s1}-\omega_{s2})$ and $(\omega_{s1}+\omega_{s2})$. This signal passes through the band pass filter 143, selects only the signal component having a frequency of $(\omega_{s1}-\omega_{s2})$, and uses the resultant signal as the reference signal of the lock-in amplifier.

An optical signal $(E_P(t))$ input to the opto-electronic converter 150 and an LO optical signal $(E_{LO}(t))$ input to the photomixer 151 along the optical paths 115, 116, 117, 118, 135, 136, 137, and 138 having the optical delays of $\tau_1$, $\tau_2$, $\tau_3$, $\tau_4$, $\tau_5$, $\tau_6$, $\tau_7$, and $\tau_8$ may be expressed by the following equation.

$$E_P(t)=A_P(e^{j((\omega_1+\omega_{s1})(t-\tau_1-\tau_5)+\varphi_{n1}[t-\tau_1-\tau_5])}+e^{j(\omega_2(t-\tau_3-\tau_5)+\varphi_{n2}[t-\tau_3-\tau_5])})$$

$$E_{LO}(t)=A_{LO}(e^{j(\omega_1(t-\tau_2-\tau_8)+\varphi_{n1}[t-\tau_2-\tau_8])}+e^{j((\omega_2-\omega_{s2})(t-\tau_4-\tau_8)+\varphi_{n2}[t-\tau_4-\tau_8])})$$ [Equation 1]

$A_P$ and $A_{LO}$ are respectively the amplitudes of the optical signals amplified by the first and second optical amplifiers 130 and 131, $\omega_1$ is the frequency of the laser light generated by the first light source unit, $\omega_2$ is the frequency of the laser light generated by the second light source unit, $\omega_{s1}$ is the frequency shifted by the first electro-optic phase modulator, $\omega_{s2}$ is the frequency shifted by the second electro-optic phase modulator, $\phi_{nm}[t]$ (m=1,2) is the phase noise included in the input laser optical signals of the first and second light source units, and $\tau_1$ to $\tau_8$ are the effective optical delay times appearing in each optical path.

The terahertz wave generated by the opto-electronic converter passes through the sample and reaches the photomixer 151 again. The terahertz wave is mixed again with the beat frequency of the LO optical signal by the photomixer 151, and electrical signals having various frequencies generated by photomixing are generated. Only the low-frequency signal having the frequency component $(\omega_{s1}-\omega_{s2})$ among the electrical signals is amplified by the trans-impedance amplifier 152 having a narrow frequency bandwidth and is output as the measurement signal of the lock-in amplifier. When considering that the shift frequencies of the electro-optic phase modulators are $\omega_{s1}$ and $\omega_{s2}$, the output $V_{TIA}(t)$ of the trans-impedance amplifier may be expressed by the following equation.

$$V_{TIA}(t) \propto \quad \text{[Equation 2]}$$

$$A_5 \cos \begin{pmatrix} \omega_s t + \phi_s - \omega_{s1}\tau_{15} + \omega_{s2}\tau_{48} - \omega_1(\tau_{15} - \tau_{28}) + \\ \omega_2(\tau_{35} - \tau_{48}) + \varphi_{n1}[t - \tau_{15}] - \varphi_{n1}[t - \tau_{28}] - \\ \varphi_{n2}[t - \tau_{35}] + \varphi_{n2}[t - \tau_{48}] \end{pmatrix}$$

$\omega_s$ is the shift frequency difference ($\omega_s = \omega_{s1} - \omega_{s2}$), and $A_s$ and $\Phi_s$ are respectively the attenuation and the phase delay caused by each sample. $\tau_{mk} = \tau_m + \tau_k$, and $\tau_{mk}$ is the effective optical delay time occurring when the light travels along the optical path of $\tau_m$ and the optical path of $\tau_k$.

In the embodiment of the present invention, in order to generate the signal having the same phase noise as the signal generated by the photomixer 151, a portion of two optical signals input to the opto-electronic converter and the photomixer is transferred as the input of the photodetector 140. When considering the difference of the optical path connected to the photodetector 140, the optical signal input to the photodetector 140 may be expressed by the following equation. In this case, it is assumed that the amplitudes $A_P$ and $A_{LO}$ of the optical signal are equal to those of the two optical signals input to the opto-electronic converter and the photomixer.

$$E_{PD}(t) = A_P(e^{j((\omega_1 + \omega_{s1})(t - \tau_1 - \tau_6) + \varphi_{n1}[t - \tau_1 - \tau_6])} + e^{j(\omega_2(t - \tau_3 - \tau_6) + \varphi_{n2}[t - \tau_3 - \tau_6])}) + A_{LO}(e^{j(\omega_1(t - \tau_2 - \tau_7) + \varphi_{n1}[t - \tau_2 - \tau_7])} + e^{j((\omega_2 - \omega_{s2})(t - \tau_4 - \tau_7) + \varphi_{n2}[t - \tau_4 - \tau_7])})$$

[Equation 3]

Then, electrical signals having various frequencies exist in the output signal $V_{PD}(t)$ of the photodetector, but the signal component having a high frequency is removed because the frequency bandwidth of the photodetector is low. Consequently, the low-frequency signal remains and this may be expressed by the following equation.

$$V_{PD}(t) \propto V_{offset} + \cos(\omega_{s1}(t - \tau_{16}) - \omega_1(\tau_{16} - \tau_{27}) + \varphi_{n1}[t - \tau_{16}] - \varphi_{n2}[t - \tau_{27}]) + \cos(\omega_{s2}(t - \tau_{47}) - \omega_2(\tau_{36} - \tau_{47}) + \varphi_{n1}[t - \tau_{36}] - \varphi_{n2}[t - \tau_{47}])$$

[Equation 4]

$V_{offset}$ is the signal of the DC component that is in proportion to the intensity of the input optical signal. After the DC component of the output signal of the photodetector is removed through the high pass filter, the output signal of the photodetector is squared through the electrical mixer and converted into an electrical signal $V_M(t)$ expressed as follows.

$$V_M(t) = (V_{PD}(t))^2 \propto V_{DC} + \quad \text{[Equation 5]}$$

$$\cos \begin{pmatrix} \omega_{s1}(t - \tau_{16}) + \omega_{s2}(t - \tau_{47}) - \omega_1(\tau_{16} - \tau_{27}) - \\ \omega_2(\tau_{36} - \tau_{47}) + \varphi_{n1}[t - \tau_{16}] - \varphi_{n2}[t - \tau_{27}] + \\ \varphi_{n1}[t - \tau_{36}] - \varphi_{n2}[t - \tau_{27}] \end{pmatrix} +$$

$$\cos \begin{pmatrix} \omega_{s1}(t - \tau_{16}) - \omega_{s2}(t - \tau_{47}) - \omega_1(\tau_{16} - \tau_{27}) + \\ \omega_2(\tau_{36} - \tau_{47}) + \varphi_{n1}[t - \tau_{16}] - \varphi_{n2}[t - \tau_{27}] - \\ \varphi_{n1}[t - \tau_{36}] + \varphi_{n2}[t - \tau_{47}] \end{pmatrix}$$

It can be seen that the above signal is composed of three terms, i.e., the DC component and the frequency components ($\omega_{s1} - \omega_{s2}$) and ($\omega_{s1} + \omega_{s2}$). Only the frequency component corresponding to the ($\omega_{s1} - \omega_{s2}$) frequency term may be derived from the signal by using the band pass filter, and the derived signal $V_{BPF}(t)$ may be expressed by the following equation.

$$V_{BFP}(t) = BPF((V_{PD}(t))^2) \propto \quad \text{[Equation 6]}$$

$$\begin{pmatrix} \Delta\omega_s(t) - \omega_{s1}\tau_{16} + \omega_{s2}\tau_{47} - \omega_1(\tau_{16} - \tau_{27}) + \\ \omega_2(\tau_{36} - \tau_{47}) + \varphi_{n1}[t - \tau_{16}] - \varphi_{n2}[t - \tau_{27}] - \\ \varphi_{n1}[t - \tau_{36}] + \varphi_{n2}[t - \tau_{47}] \end{pmatrix}$$

The signal $V_{BPF}(t)$ passing through the band pass filter has the same frequency as $V_{TIA}(t)$ obtained through the trans-impedance amplifier and expressed by Equation 2, and the phase component is composed of the phase delay and the phase noise. In this case, when it is assumed that the two optical paths 135 and 136 connected to the first optical amplifier 130 have the same delay time and the two optical paths 137 and 138 connected to the second optical amplifier 131 have the same delay time, the signal $V_{BPF}(t)$ passing through the band pass filter and the signal $V_{TIA}(t)$ obtained through the trans-impedance amplifier have the same phase noise.

The two signals are input to the lock-in amplifier 153. At this time, the signal $V_{TIA}(t)$ passing through the trans-impedance amplifier is set as the measurement signal and the signal $V_{BPF}(t)$ passing through the band pass filter is set as the reference signal. Then, the phase noise included in the optical signal may be removed by mathematically subtracting the phase components of the two signals through the lock-in process.

According to the embodiment, in order to set the two signals to have the same phase noise, the optical signal amplified by the first optical amplifier 130 is distributed and transferred to the photodetector 140 and the opto-electronic converter 150, and the optical path 136 formed between the first optical amplifier 130 and the photodetector 140 may be set to have the same optical delay time as that of the optical path 135 formed between the first optical amplifier 130 and the photomixer 150 that the optical signal converted into the terahertz wave through the opto-electronic converter reaches.

Similarly, the optical signal amplified by the second optical amplifier 131 is distributed and transferred to the photodetector 140 and the photomixer 151, and the optical path 137 formed between the second optical amplifier 131 and the photodetector 140 may be set to have the same optical delay as that of the optical path 138 formed between the second optical amplifier and the photomixer 150.

Therefore, the lengths of the optical lines are set so that the electrical signal transferred from the trans-impedance amplifier to the lock-in amplifier and the electrical signal filtered by the band pass filter and transferred to the lock-in amplifier have the same frequency and phase noise, and thus, the two electrical signals have the same phase noise. It is possible to obtain phase information in which the phase noise is removed from the signal obtained by the trans-impedance converter 152 through the lock-in process.

In order to remove the phase noise, the conventional photomixing-based terahertz wave system must set the lengths of the optical paths by taking into account the effective optical delay characteristics of the optical components, such as the photomixer, the light splitter, the frequency shifter, and the optical amplifier. However, according to the present invention, only the lengths of the optical paths 135, 136, 137, and 138 connected to the optical amplifier are just adjusted. Since other optical components are not present between the optical paths, the lengths of the optical paths may be more easily set to remove the phase noise included in the continuous-wave laser light source.

Figure 2:
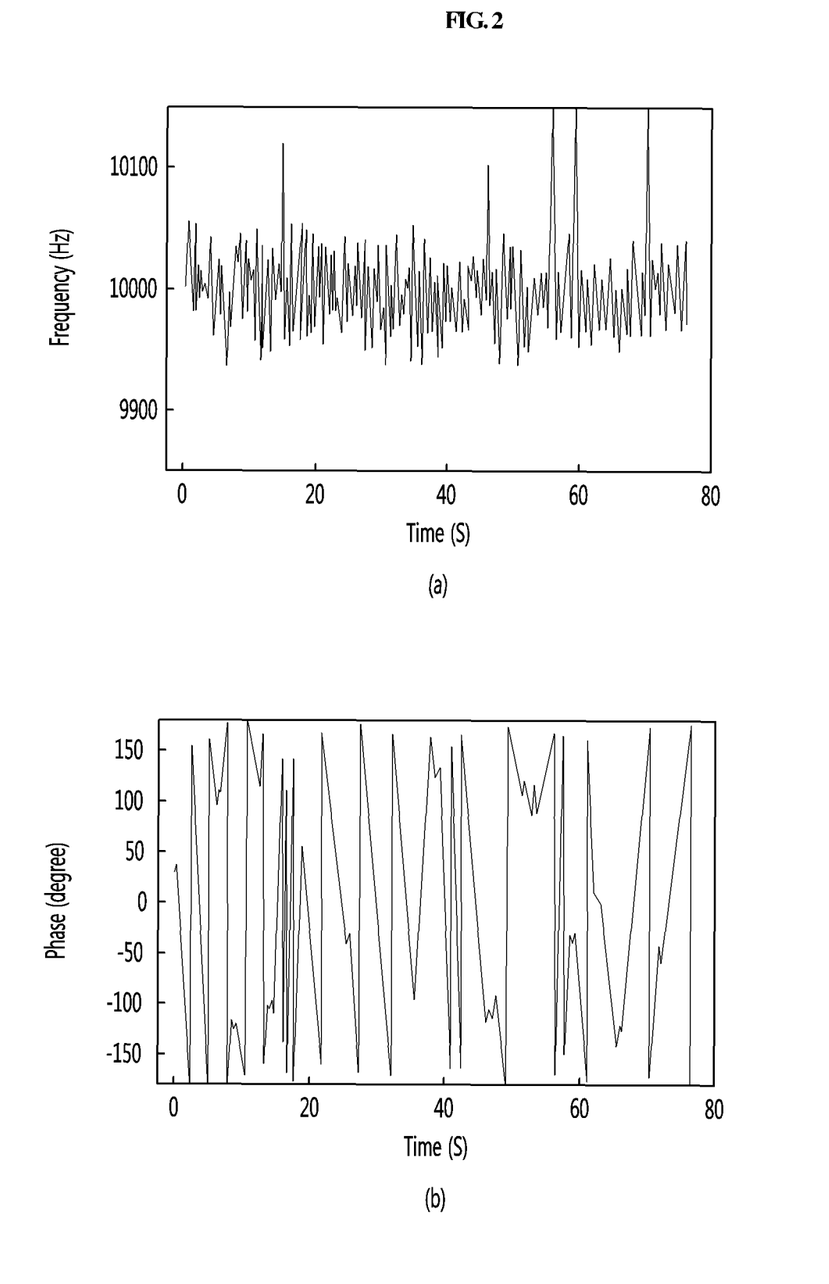
FIG. 2 is a diagram illustrating a frequency shift of an output signal of a photomixer and a phase response of a lock-in amplifier, which are generated by phase noise of a laser light source in a continuous-wave terahertz generation and detection device according to the related art.
Figure 3:
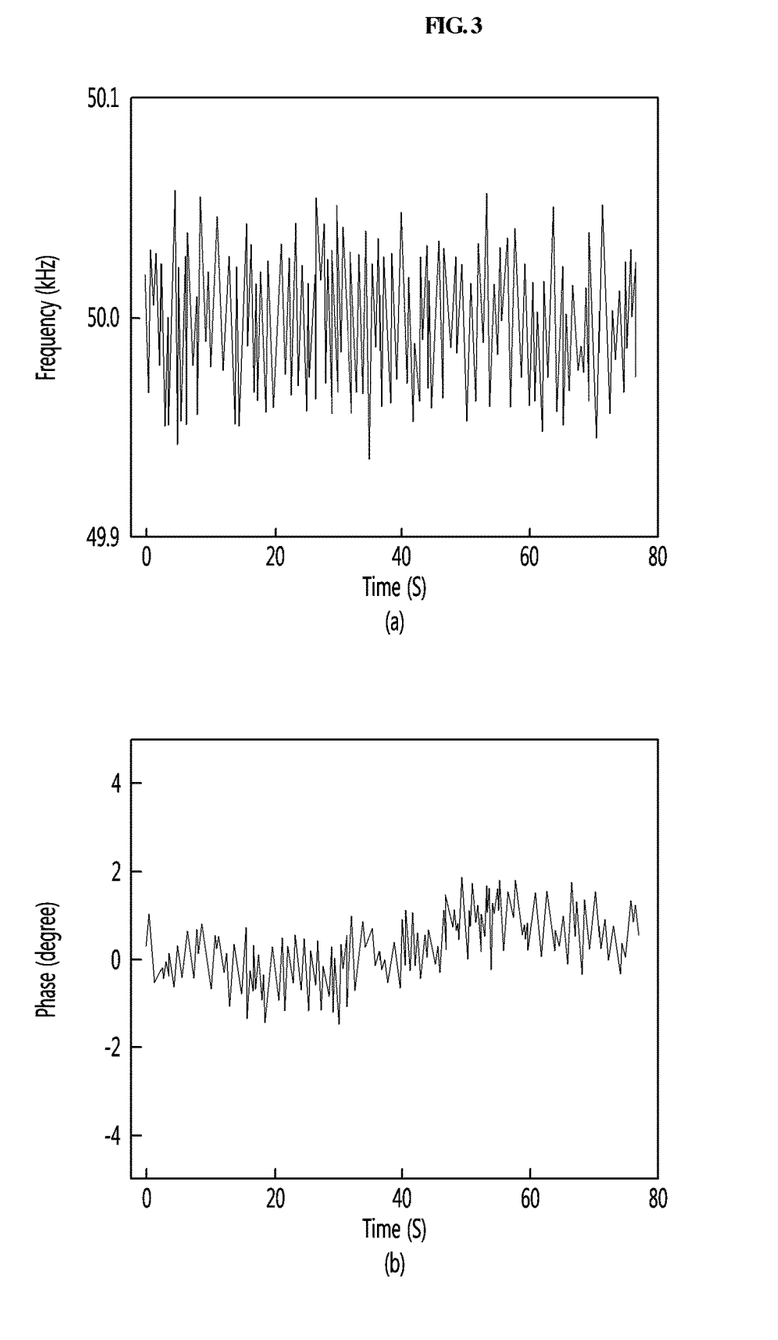
FIG. 3 is a diagram illustrating a frequency shift of an output signal of a photomixer and a phase response of a lock-in amplifier, which are generated by phase noise of a laser light source in a continuous-wave terahertz generation and detection device according to an embodiment of the present invention.

FIG. 2 is a diagram illustrating a frequency shift caused by laser phase noise and a phase response of a lock-in amplifier in the conventional terahertz wave system, and FIG. 3 is a diagram illustrating a frequency shift caused by laser phase noise and a phase response of a lock-in amplifier in the continuous-wave terahertz generation and detection device according to an embodiment of the present invention.

A measurement value of FIG. 2 was obtained by measuring characteristics of the conventional continuous-wave terahertz generation and detection device except for the part indicated by the dashed line in FIG. 1. In order to minimize the phase noise in manufacturing the system, the lengths of two effective optical lines were adjusted to be maximally equal to each other. However, even when the lengths of the optical lengths were adjusted for removing the phase noise, different optical components exist in the two optical lines and there exists a length error of the optical path due to a manufacturing error of optical components such as optical fibers used therein. As a result, very great frequency shift and phase shift occur as illustrated in FIG. 2.

More specifically, it can be seen from FIG. 2 that the influence of the phase noise is not completely removed by such optical path adjustment error in the conventional continuous-wave terahertz generation and detection device, and thus, the frequency of the output signal of the trans-impedance amplifier 152 is randomly changed. At this time, when the signal having a frequency corresponding to the modulation frequency difference ($\omega_s$) is used as the reference frequency of the lock-in amplifier, the phase response of the lock-in amplifier is randomly changed.

A measurement value of FIG. 3 was obtained by measuring characteristics of the continuous-wave terahertz generation and detection device including the part indicated by the dashed line in FIG. 1. Parts other than the part indicated by the dashed line are the same as the configuration of the conventional system. In the continuous-wave terahertz generation and detection device of FIG. 3 according to the embodiment, although the frequency of the output signal of the trans-impedance amplifier 152 is randomly changed by the influence of the phase noise generated by the optical path adjustment error, but the frequency of the output signal of the trans-impedance amplifier 152 is changed in the same shape because the output signal of the band pass filter 143 used as the reference frequency of the lock-in amplifier has the same phase noise. Therefore, the phase noise component is removed from the phase response characteristics obtained by the lock-in amplifier, and thus, the output signal value is constantly maintained. That is, it can be confirmed that the continuous-wave terahertz generation and detection device according to the embodiment can easily remove the phase noise without precisely adjusting the optical paths.

Figure 4:
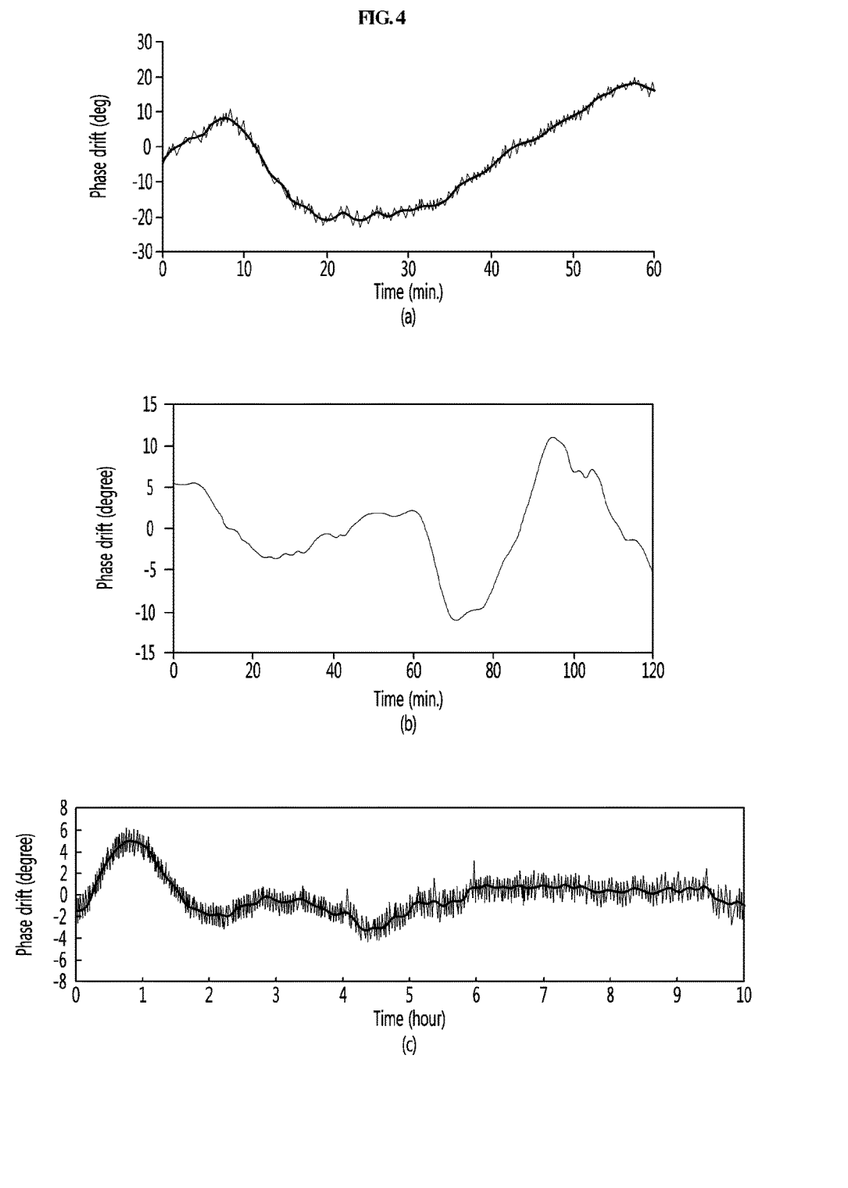
FIG. 4 is a diagram illustrating changes in phase response according to a change in ambient temperature in the continuous-wave terahertz generation and detection device according to the related art and the continuous-wave terahertz generation and detection device according to the embodiment of the present invention.

FIG. 4 is a diagram illustrating changes in phase response according to a change in ambient temperature in the continuous-wave terahertz generation and detection device according to the related art and the continuous-wave terahertz generation and detection device according to the embodiment of the present invention. When a temperature changes, the length of the effective optical line changes due to various factors, thus causing a phase change. In order to reduce such influence, the conventional photomixing-based continuous-wave terahertz generation and detection device uses a method of maximally reducing the length of the entire optical paths and thermally insulating the entire system. (a) of FIG. 4 illustrates a change in phase response according to a change in a temperature of a system in which the lengths of the optical paths 115, 116, 117, and 118 was minimized to 40 cm so as to reduce the influence of the temperature change in the conventional continuous-wave terahertz generation and detection device, (b) of FIG. 4 illustrates a change in phase response according to a change in a temperature of a system in which the optical paths 115, 116, 117, and 118 were integrated in a size of 2 mm×2 mm through optical integrated circuit technology, and (c) of FIG. 4 illustrates a change in phase response according to a temperature change in the embodiment of the present invention.

Referring to (a) to (c) of FIG. 4, the continuous-wave terahertz generation and detection device according to the embodiment as illustrated in (c) showed a more excellent result in terms of phase stability, as compared with the case in which the lengths of the optical paths were reduced as illustrated in (a). Also, as compared with the case of using the optical integrated circuit for reducing the length of the portion where the optical lines are divided as illustrated in (b), the variation width of the phase according to the time in (c) of the embodiment was measured to be lower, thereby showing a more excellent result in terms of phase stability.

Since the existing continuous-wave terahertz generation and detection device using the photomixing technique uses an expensive continuous-wave laser light source having a narrow bandwidth so as to obtain a stable phase response, the continuous-wave laser light source occupies a large portion of the device in terms of system design costs. However, according to the present embodiment, an expensive continuous-wave laser light source having a narrow bandwidth need not be used, and the influence of the phase noise due to the laser can be reduced by additionally configuring one photodetector whose frequency bandwidth is not large and the electronic circuit connected to the photodetector. Therefore, since system design costs can be reduced and the operation of adjusting the lengths of the optical paths is simplified, it is advantageous to system design. Also, it is possible to provide the continuous-wave terahertz generation and detection device that is not sensitive to the change in the temperature of the ambient environment, without using additional devices.

Although the embodiments have been mainly described above, they are just exemplary and do not limit the present invention. Thus, those skilled in the art to which the present invention pertains will know that various modifications and applications which have not been exemplified may be carried out within a range which does not deviate from the essential characteristics of the embodiments. For instance, the constituent elements described in detail in the exemplary embodiments can be modified to be carried out. Further, the differences related to such modifications and applications shall be construed to be included in the scope of the present invention specified in the attached claims.

INDUSTRIAL APPLICABILITY

According to the present invention, since the phase noise caused by the continuous-wave laser light source can be reduced by just adding one photodetector and an electronic circuit, the continuous-wave terahertz generation and detection device can be implemented by using a relatively inexpensive laser. Therefore, industrial applicability of the present invention is greatly expected.

The invention claimed is:
1. A continuous-wave terahertz generation and detection device comprising:
first and second light source units configured to provide laser lights, which have single wavelength and different frequencies, to generate optical signals;

a first electro-optic phase modulator configured to shift a frequency of the optical signal generated by the first light source unit, and a second electro-optic phase modulator configured to shift a frequency of the optical signal generated by the second light source unit;

a first optical amplifier configured to receive and amplify the optical signal whose frequency is shifted by the first electro-optic phase modulator and the optical signal generated by the second light source unit, and a second optical amplifier configured to receive and amplify the optical signal whose frequency is shifted by the second electro-optic phase modulator and the optical signal generated by the first light source unit;

an opto-electronic converter configured to convert the optical signal amplified by the first optical amplifier into a terahertz wave;

a photomixer configured to mix the optical signal input from the second optical amplifier and the terahertz wave generated by the opto-electronic converter and convert the mixed signal into an electrical signal;

a photodetector configured to combine the optical signals transferred from the first and second optical amplifiers and convert the combined optical signal into an electrical signal; and a filter unit configured to filter the electrical signal passing through the photodetector, wherein the electrical signal obtained through the photodetector is compared with the electrical signal obtained by the photomixer, and phase noise having the same frequency is removed.

2. The continuous-wave terahertz generation and detection device of claim 1, wherein the optical signal amplified by the first optical amplifier is distributed and transferred to the photodetector and the opto-electronic converter, and an optical path formed between the first optical amplifier and the photodetector is set to have the same effective optical delay time as that of an optical path formed between the first optical amplifier and the opto-electronic converter.

3. The continuous-wave terahertz generation and detection device of claim 1, wherein the optical signal amplified by the second optical amplifier is distributed and transferred to the photodetector and the photomixer, and an optical path formed between the second optical amplifier and the photodetector is set to have the same effective optical delay time as that of an optical path formed between the second optical amplifier and the photomixer.

4. The continuous-wave terahertz generation and detection device of claim 1, wherein the filter unit connected to the photodetector comprises a high pass filter, and the high pass filter removes a signal of DC component from the electrical signal transferred from the photodetector.

5. The continuous-wave terahertz generation and detection device of claim 4, wherein the filter unit comprises an electrical mixer connected to the high pass filter, and the electrical mixer performs a square operation on the signal filtered by the high pass filter.

6. The continuous-wave terahertz generation and detection device of claim 5, wherein the filter unit comprises a band pass filter connected to the electrical mixer, and the band pass filter passes only a signal having a relatively low frequency, which is included in the electrical signal output from the photomixer, by removing a signal of DC and high-frequency components from the electrical signal output from the electrical mixer.

7. The continuous-wave terahertz generation and detection device of claim 6, comprising a trans-impedance amplifier connected to the photomixer, wherein the trans-impedance amplifier amplifies the electrical signal output from the photomixer.

8. The continuous-wave terahertz generation and detection device of claim 7, comprising a lock-in amplifier connected to the trans-impedance amplifier and the band pass filter, wherein the lock-in amplifier performs mathematical subtraction to remove phase noise of the electrical signal transferred through the trans-impedance amplifier and the electrical signal transferred through the photodetector and the band pass filter.

9. The continuous-wave terahertz generation and detection device of claim 8, wherein lengths of optical lines are set so that the electrical signal transferred from the trans-impedance amplifier and the electrical signal filtered by the band pass filter have the same frequency and phase noise.

* * * * *